US006284709B1

(12) United States Patent
Ju et al.

(10) Patent No.: US 6,284,709 B1
(45) Date of Patent: Sep. 4, 2001

(54) COMPOSITION FOR STIMULATING PLANT GROWTH AND FOR IMPROVING PLANT PRESERVATION AND METHOD FOR PREPARING THE SAME

(75) Inventors: Jong Gon Ju, Kyunggi-do; Jong Ho Koh; Woong Whan Yi, both of Seoul, all of (KR)

(73) Assignee: Nel Biotech Co., Ltd., Kyunggi-do (KR)

( * ) Notice: Subject to any disclaimer, the term of this patent is extended or adjusted under 35 U.S.C. 154(b) by 0 days.

(21) Appl. No.: 09/513,924

(22) Filed: Feb. 28, 2000

(30) Foreign Application Priority Data

Apr. 30, 1999 (KR) ........................................ 99-15577

(51) Int. Cl.[7] .............................. A01N 3/00; A01N 43/08; A01N 59/00; C05D 11/00

(52) U.S. Cl. .......................... 504/123; 504/292; 504/299; 71/61; 71/62; 71/63

(58) Field of Search .................................... 504/292, 299, 504/123; 71/61, 62, 63

(56) References Cited

U.S. PATENT DOCUMENTS 5,230,822 * 7/1993 Kamel et al. .......................... 252/95
5,374,369 * 12/1994 Angevaare et al. .................. 252/95

* cited by examiner

*Primary Examiner*—S. Mark Clardy
(74) *Attorney, Agent, or Firm*—McDermott, Will & Emery

(57) ABSTRACT

Disclosed is a composition useful for plant growth and vegetable preservation, comprising 2.25–5.13 moles of potassium silicate, 0.25–0.57 moles of sodium silicate and/or sodium hydroxy silicate, 1.98–5.59 moles of potassium carbonate, 0.22–0.51 moles of sodium carbonate and/or sodium bicarbonate, 0.25–0.75 moles of potassium chloride; and 0.45–0.84 moles of a reducing sugar. It can be prepared by solubilizing the components at such amounts in 1 liter of distilled water maintained at 80–90 ° C. through a sol-gel process, stirring the solution under the inflow of air while reducing the temperature of the solution to 18–90° C. at a rate of 4–6° C. per min, and allowing the resulting sol-gel phase to stand at room temperature for 24–36 hours. The composition stimulates the growth of plants as well as builds up the disease endurance of vegetables through its activity against plant bacteria. Also, it can restrain the soil from being acidified. It is safe to the body while having beneficial effects on agricultural products, including preservation extension, bacteria growth inhibition and texture sense improvement.

3 Claims, No Drawings

COMPOSITION FOR STIMULATING PLANT GROWTH AND FOR IMPROVING PLANT PRESERVATION AND METHOD FOR PREPARING THE SAME

FIELD OF THE INVENTION

The present invention relates to a composition for stimulating plant growth and for improving plant preservation. More particularly, the present invention relates to a composition based on alkaline earth ionized minerals, which has functions of stimulating plant growth, improving vegetable preservation, building up vegetable disease endurance, inhibiting bacterial propagation and improving soil fertility with safety to the body.

BACKGROUND OF THE INVENTION

Recent aggravation of air pollution and soil pollution has rapidly acidified growth conditions of plants. Also, such pollution seriously inhibits the growth and activity of microbes that inhabit soils, resulting in a significant decrease of soil fertility.

In addition, overuse of agricultural chemicals causes serious medical and social problems. For example, in Korea, hundreds of farmers are directly poisoned causing significant health problems or even resulting in death by agricultural chemicals. What is worse, a multitude of consumers are also threatened by the agricultural products contaminated with chemicals. In fact, nowadays, the agricultural products, which are usually eaten, are frequently reported to be sold at markets while being contaminated with chemicals. Further, contamination of streams with agricultural products destructive to their ecosystems, causing pollution-related diseases.

Referring to a survey of the Korea Consumer Protection Board, methyl thiophene was detected at an amount of 0.2–7.7 ppm in some bean sprouts which were sold unpacked in Korea. This agricultural chemical is a precursor of cabendazim, a compound of carcinogenicity and teratogenicity. That is, a modified form of methyl thiophene may cause cancers or childbirth abnormalities. Thiophanate methyl is a main ingredient of Homai, an agricultural chemical which is typically used to wash various seeds, such as rice seeds, onion seeds, bean seeds, sesame seeds, before seeding. However, thiophanate methyl is legally prohibited from being used for the cultivation of bean sprouts as it is decomposed into cabendazim by the metabolism of bean sprouts themselves. Because Homai can prevent the putrefaction and discoloration of bean sprouts during their cultivation in addition to washing the seeds, it may be used before seeding and during cultivation.

Typical factors to shorten distribution periods of agricultural products include microbe-causing putrefaction, oxidization, and enzyme-causing quality degradation. Thus, to improve the preservation of agricultural products, antimicrobial agents and/or antioxidants are employed. As a result of such synthesis chemicals, including antimicrobial chemicals and growth-stimulating chemicals, it is not too much to say that almost all of the foods people usually eats are contaminated with agricultural chemicals.

Nutritionally comparing with meats, beans are rich in proteins and lipids. In particular, bean sprouts, which are germinated from beans, are a very popular food material and serve as a nutrition source in Korea. During the cultivation of bean sprouts, treatment with growth-stimulating agents reduces their average height by about 35% while making their hypocotyl parts thicker by about 40%. Such chemocultivation of bean sprouts, however, suffers from a serious problem in that chemicals remain in the food and thus, threaten the health of the consumers.

In order to solve such problems, various seed germination and plant growth stimulants of low toxicity have been developed. For instance, Korean Pat. Laid-Open Publication No. 95-702387 suggests laminarin as a stimulating agent for seed germination and plant growth. In Korean Pat. Laid-Open Publication No. 84-3383, there is disclosed a plant growth controlling agent which comprises at least one substituted naphthalene in addition to 1,4- and 1,6-dimethyl naphthalene, and an inert carrier or diluent. Another plant growth controlling agent can be referred to Korean Pat. Laid-Open Publication No. 88-12159 in which dialkylimidazolyl phosphate and dialkylimidazolyltetraraphosphoate are used as main ingredients. These compounds disclosed in the above-cited references, however, are synthetic compounds which cannot guarantee their safety to the human body. Korean Pat. Laid-Open Publication discloses a composition comprising elvan, phosphorite, glauconite and magnesite, asserting that it acts to improve soil fertility and stimulate plant growth. However, this composition is poor in such effects.

SUMMARY OF THE INVENTION

Leading to the present invention, the extensive and thorough research on an agent for improving the growth and preservation of plants, repeated by the present inventors aiming to apply the agent to vegetables with safety to the body, resulted in the finding that an ionized combination of potassium compounds, sodium compounds and silicon compounds can stimulate the growth of plants as well as extend the preservation of vegetables without producing any toxicity to the human body. In addition, this stimulative and preservative agent was found to improve the texture senses and thus, the food value of vegetables. Consequently, this agent guarantees safe agricultural products with economical lucrativeness.

Therefore, it is an object of the present invention to provide an alkaline earth ionized mineral composition which is safe to the body and has functions of stimulating plant growth, improving vegetable preservation, building up vegetable disease endurance, inhibiting bacterial propagation and improving soil fertility.

It is another object of the present invention to provide a method for preparing the composition.

It is a further object of the present invention to provide the use of the composition in improving the growth and the preservation of bean plants.

In an aspect of the present invention, there is provided a composition for stimulating plant growth and for improving vegetable preservation, comprising per liter of distilled water: 2.25–5.13 moles of potassium silicate; 0.25–0.57 moles of a compound selected from the group consisting of sodium silicate, sodium hydroxy silicate and the mixture thereof; 1.98–5.59 moles of potassium carbonate; 0.22–0.51 moles of a compound selected from the group consisting of sodium carbonate, sodium bicarbonate and the mixture thereof; 0.25–0.75 moles of potassium chloride; and 0.45–0.84 moles of a reducing sugar.

In accordance with another aspect of the present invention, there is provided a method for preparing the composition, comprising the steps of: solubilizing the above components at predetermined amounts in 1 liter of distilled water maintained at 80–90° C. through a sol-gel process; stirring the solution under the inflow of air while reducing the temperature of the solution to 18–22° C. at a rate of 4–6°

C. per min; and allowing the resulting sol-gel phase to stand at room temperature for 24–36 hours.

In accordance with a further aspect of the present invention, there is provided the use of the composition in improving the growth and the preservation of bean plants, leaf vegetables and fruit vegetables, in which the composition is used at an amount of 0.1 to 0.3%.

DETAILED DESCRIPTION OF THE INVENTION

In the present invention, a combination of potassium silicate; sodium silicate and/or sodium hydroxy silicate; potassium carbonate; sodium carbonate and/or sodium bicarbonate; potassium chloride; and a reducing sugar is used as a composition for stimulating the growth of plants and for extending the preservation of vegetables.

When being applied to vegetables, potassium silicate makes their roots, stems and leaves healthy and thus, builds up the disease endurance of the vegetables. For soils, potassium silicate is added as a factor for controlling a cation mineral metabolism. It is preferably used at an amount of 2.25–5.13 moles per liter of distilled water. For instance, if potassium silicate is used at less than 2.25 moles, the agent performs insufficient functions in building up the disease endurance of the vegetables and controlling their cation mineral metabolisms. On the other hand, when the amount of potassium silicate exceeds 5.13 moles, too great an amount of cations are accumulated in the soil.

As a controller for the physiological activity of the potassium silicate, a compound is used which is selected from the group consisting of sodium silicate, sodium hydroxy silicate, and mixtures thereof. Its amount is preferably from 0.25 to 0.57 moles per liter of distilled water. For example, if present at a concentration of less than 0.25 moles, this compound cannot play a role as the controller. On the other hand, if present at a too great amount, the controlling factor is inhibited from being operated.

In addition to promoting the carbon assimilation of plants, the potassium carbonate is used as a factor for controlling the decomposition mechanisms soil bacteria perform. Its amount in the agent of the present invention preferably ranges from 1.98 to 5.59 moles per liter of distilled water. Less than 0.22 moles of potassium carbonate is insufficient to induce plants and soil bacteria to actively perform the carbon assimilation and the decomposition mechanisms while more than 0.51 moles of potassium carbonate inhibits the normal activity of plants and soil bacteria.

Potassium chloride serves as a factor to provide disease endurance for plants. Its preferable amount is within the range of 0.25 to 0.75 moles per liter of distilled water. For example, when used at an amount of less than 0.25 moles, potassium chloride shows no beneficial effects. On the other hand, when used at an amount of greater than 0.75 moles, potassium chloride inhibits the normal growth of the plants.

Also, the composition of the present invention comprises a reducing sugar at an amount of 0.45 to 0.84 moles. Its function is to provide a reaction foundation for the mineral compounds so as to form stable complexes.

The composition of the present invention is prepared by solubilizing in 1 liter of distilled water maintained at 80–90 ° C. a composition comprising 2.23–5.13 moles of potassium silicate, 0.25–0.57 moles of a compound selected from the group consisting of sodium silicate, sodium hydroxy silicate and the mixture thereof, 1.98–5.59 moles of potassium carbonate, 0.22–0.51 moles of a compound selected from the group consisting of sodium carbonate, sodium bicarbonate and the mixture thereof, 0.25–0.75 moles of potassium chloride, and 0.45–0.84 moles of a reducing sugar through a sol-gel process, stirring the solution under the inflow of air while reducing the temperature of the solution to 18–22° C. at a rate of 4–6° C. per min, and allowing the resulting sol-gel phase to stand at room temperature for 24–36 hours. The temperature reduction at a rate of 4–6° C. is to stabilize and optimize the anion source minerals. Further, the control temperature out of the range of 18–22° C. instabilizes the formation of anion minerals.

Sodium silicate and sodium hydroxy silicate both may be used in the present invention. Alternatively, only one of them suffices the accomplishment of the present invention. In the case of selecting both of them, they are preferably used at the same equivalent. Likewise, as for sodium carbonate and sodium bicarbonate, both or any one of them may be used. When they both are selected, they are preferably used at the same equivalent.

It is preferable that the composition of the present invention is applied at 0.2–0.3% for bean sprouts and at 0.1–0.3% for fruit vegetables and leaf vegetables. However, the effective concentration may be changed according to the conditions of vegetables.

A better understanding of the present invention may be obtained in light of the following examples which are set forth to illustrate, but are not to be construed to limit the present invention.

EXAMPLE I

Preparation of Alkaline Earth Ionized Mineral Composition for Plant Growth Stimulation and Vegetable Preservation Improvement In 1 liter of distilled water maintained at 80° C., 3.7 moles of potassium silicate, 0.4 moles of sodium silicate, 3.8 moles of potassium carbonate, 0.4 moles of sodium carbonate, 0.5 moles of potassium chloride and 0.6 moles of a reducing *sugar were successively dissolved, after which the solution was stirred under an air inflow condition while the solution temperature was decreased at a rate of about 5° C. per min to about 20° C. The resulting solution was allowed to stand for stabilization at room temperature for about 30 hours to yield a gel. This gel was diluted fifteen-folds to give a sol phase of an alkaline earth ionized mineral composition for plant growth stimulation and vegetable preservation improvement.

EXAMPLE II

Preparation of Alkaline Earth Ionized Mineral Composition for Plant Growth Stimulation and Vegetable Preservation

Improvement

In 1 liter of distilled water maintained at 80° C., 3.7 moles of potassium silicate, 0.4 moles of sodium hydroxy silicate, 3.8 moles of potassium carbonate, 0.4 moles of sodium bicarbonate, 0.5 moles of potassium chloride and 0.6 moles of a reducing sugar were successively dissolved, after which the solution was stirred under an air inflow condition while the solution temperature was decreased at a rate of about 5° C. per min to about 20° C. The resulting solution was allowed to stand for stabilization at room temperature for about 30 hours to yield a gel. This gel was diluted fifteen-folds to give a sol phase of an alkaline earth ionized mineral composition for plant growth stimulation and vegetable preservation improvement.

EXAMPLE III

Effect of the Composition on Seed Germination and Plant Growth

To assay the composition of the present invention for seed germination and plant growth, the composition obtained in Example I was used at amounts of 0.1–0.5% for the cultivation of bean sprouts. As a control, bean sprouts were cultured with no agents. The bean sprouts were measured for height, thickness and weight and the results are given in Table 1, below. As seen in Table 1, the composition of the present invention is useful for the cultivation of bean sprouts and its effective amount ranges from 0.2 to 0.3%.

TABLE 1

Effect of the Composition on the Cultivation of Bean Sprout

| Test Items | Amounts (%) | | Culture Period (day) 0 | 1 | 2 | 3 | 4 |
|---|---|---|---|---|---|---|---|
| Length (cm) | Control | | 0 | 2.5 | 5.0 | 12.0 | 16.0 |
| | Composition | 0.1 | 0 | 2.5 | 5.0 | 12.0 | 16.0 |
| | | 0.2 | 0 | 4.0 | 7.8 | 15.2 | 18.5 |
| | | 0.3 | 0 | 4.0 | 7.8 | 16.0 | 21.5 |
| | | 0.5 | 0 | 3.9 | 7.7 | 15.8 | 20.0 |
| Thickness (mm) | Control | | 0 | 0.85 | 2.00 | 2.00 | 1.70 |
| | Composition | 0.1 | 0 | 0.85 | 1.95 | 2.00 | 1.95 |
| | | 0.2 | 0 | 1.00 | 1.95 | 2.10 | 2.00 |
| | | 0.3 | 0 | 1.00 | 2.00 | 2.00 | 1.90 |
| | | 0.5 | 0 | 1.00 | 2.00 | 1.95 | 1.90 |
| Weight (g) | Control | | 0 | 15 | 30 | 54 | 55 |
| | Composition | 0.1 | 0 | 16 | 34 | 48 | 53 |
| | | 0.2 | 0 | 20 | 42 | 58 | 68 |
| | | 0.3 | 0 | 19 | 39 | 56 | 75 |
| | | 0.4 | 0 | 19 | 38 | 55 | 73 |

EXAMPLE IV

Comparison with Growth Stimulating Agricultural Chemicals

The composition obtained in Example II was used at 0.25% for the cultivation of bean sprouts. For comparison, bean sprouts were cultured by use of Indolbi, a growth stimulating agent for bean sprouts, manufactured by Young Il Chemicals, Korea, and Homai, which is usually used to extend the distribution period of bean sprouts, manufactured by JinJin Industries, Korea. Separately, a combination of the composition of the present invention and Indolbi was applied for the cultivation of bean sprouts. As a control, bean sprouts were grown without any chemicals. Each of the samples was measured for height, thickness and weight and the results are given in Table 2, below.

TABLE 2

Effects of Various Agents on the Growth of Bean Sprouts

| Test Items | Amounts (%) | Culture Period (day) 0 | 2 | 3 | 5 |
|---|---|---|---|---|---|
| Length (cm) | Control | 0 | 7.5 | 13.0 | 17.5 |
| | Composition 0.25 | 0 | 7.5 | 13.5 | 21.5 |
| | Composition 0.25 + Indolbi | 0 | 6.5 | 10.0 | 16.0 |
| | Homai + Indolbi | 0 | 6.5 | 12.0 | 16.1 |
| Thickness (mm) | Control | 0 | 2.1 | 1.8 | 1.7 |
| | Composition 0.25 | 0 | 2.1 | 1.9 | 1.8 |
| | Composition 0.25 + Indolbi | 0 | 2.5 | 2.3 | 2.3 |
| | Homai + Indolbi | 0 | 2.4 | 2.2 | 2.2 |

TABLE 2-continued

Effects of Various Agents on the Growth of Bean Sprouts

| Test Items | Amounts (%) | Culture Period (day) 0 | 2 | 3 | 5 |
|---|---|---|---|---|---|
| Weight (g) | Control | 0 | 36 | 48 | 68 |
| | Composition 0.25 | 0 | 43 | 53 | 78 |
| | Composition 0.25 + Indolbi | 0 | 43 | 57 | 82 |
| | Homai + Indolbi | 0 | 43 | 60 | 83 |

As apparent from the data, the composition of the present invention is very useful to culture bean sprouts without producing toxicity. Bean sprouts were the fastest grown when only the composition of the invention was used. In the improvement in the thickness and weight of bean sprouts, the composition of the invention is superior to the control group, but poor compared with the agricultural chemical groups. However, the difference between the composition of the invention and the chemical groups is not so large and thus, tolerable when account is taken of the safety of the composition to the human body.

EXAMPLE V

Inhibitory Effects Against Microbial Propagation During Storage

During storage at 6° C., the bean sprouts cultured with the help of the composition obtained in Example I were observed for bacterial propagation, along with the control group and the agricultural chemical groups. The results are given in Table 3, below.

TABLE 3

Inhibitory Effects Against Microbial Propagation During Storage

Unit: CFU/g

| Amounts (%) | Culture Period (day) 0 | 3 | 6 | 9 | 12 | 15 |
|---|---|---|---|---|---|---|
| Control | 6.2 | 6.4 | 6.7 | 7.2 | 7.5 | 8.2 |
| Composition 0.25 | 6.0 | 6.2 | 6.4 | 8.2 | 7.0 | 7.4 |
| Composition 0.25 + Indolbi | 6.8 | 7.3 | 7.9 | 6.5 | 8.7 | 9.2 |
| Homai + Indolbi | 5.7 | 6 | 6.3 | 6.4 | 6.7 | 7.0 |

As shown in Table 3, the composition of the invention is slightly inferior to the Homai and Indolbi group, but superior to the control group in the antimicrobial effect. So, the composition of the invention is very useful for the preservation of bean sprouts.

EXAMPLE VI

Effect on Physical Properties

Bean sprouts were cultured for four days with the help of the composition of the present invention, a combination of the composition and Indolbi, and a combination of Homai and Indolbi, and without using any agents, as in Example III. From each group of the cultured bean sprouts, 50 samples were randomly selected, and an examination was made of their physical properties and texture sense. In this regard, the samples were measured for cutting strength before and after being cooked. The results are given in Table 4, below. As seen, the composition of the invention can afford excellent texture sense to bean sprouts.

TABLE 4

| Change in Texture Sense Before and After Cooking of Bean Sprouts | | |
|---|---|---|
| | Cutting Strength (g) | |
| Amounts (%) | Before Cooking | After Cooking |
| Control | 320 | 630 |
| Composition 0.25 | 360 | 640 |
| Composition 0.25 + Indolbi | 220 | 530 |
| Homai + Indolbi | 225 | 585 |

Note: Cooking condition: 100° C., 5 min

EXAMPLE VII

Effect on Preservation of Vegetables

An examination was made of the improvement effect of the composition of the invention on the preservation of fruit vegetables, such as cucumber, strawberry, tomato and pepper, and leaf vegetables, such as lettuce. For the arrangement of the vegetables, a randomized blocks method was conducted three times. During the cultivation with the help of the composition of the invention, the vegetables were analyzed for their growth states and, after the cultivation, the effect of the composition on the preservation of the vegetables was also analyzed. The composition was used at amounts of 0.25%, 1% and 5% and, as a control, the vegetables were cultivated without using any agents. The results are given in Table 5, below. It was found that the most effective results are obtained when the composition is used at 2.5%.

TABLE 5

| Vegetables | | Preservation Improvement (%) | |
|---|---|---|---|
| | | 20 ± 2° C. | 10 ± 2° C. |
| Fruit Vegetables | Cucumber | 15 | 8 |
| | Strawberry | 20 | 15 |
| | Tomato | 15 | 10 |
| | Pepper | 10 | 5 |
| Leaf Vegetable | Lettuce | 30 | 18 |

As described hereinbefore, the alkaline earth ionized mineral composition according to the present invention stimulates the growth of plants as well as builds up the disease endurance of vegetables through its activity against plant bacteria. In addition, the composition can restrain the soil from being acidified. What is more important, the composition is safe to the body while having beneficial effects on agricultural products, including preservation extension, bacteria growth inhibition (putrefaction retardance) and texture sense (texture elasticity) improvement.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A composition for stimulating plant growth and for improving vegetable preservation, comprising per liter of distilled water:

2.25–5.13 moles of potassium silicate;

0.25–0.57 moles of a compound selected from the group consisting of sodium silicate, sodium hydroxy silicate and the mixture thereof;

1.98–5.59 moles of potassium carbonate;

0.22–0.51 moles of a compound selected from the group consisting of sodium carbonate, sodium bicarbonate and the mixture thereof;

0.25–0.75 moles of potassium chloride; and 0.45–0.84 moles of a reducing sugar.

2. A method for preparing a composition for stimulating plant growth and for improving vegetable preservation, comprising the steps of:

solubilizing in 1 liter of distilled water maintained at 80–90° C. a composition comprising 2.23–5.13 moles of potassium silicate, 0.25–0.57 moles of a compound selected from the group consisting of sodium silicate, sodium hydroxy silicate and the mixture thereof, 1.98–5.59 moles of potassium carbonate, 0.22–0.51 moles of a compound selected from the group consisting of sodium carbonate, sodium bicarbonate and the mixture thereof, 0.25–0.75 moles of potassium chloride, and 0.45–0.84 moles of a reducing sugar through a sol-gel process;

stirring the solution under the inflow of air while reducing the temperature of the solution to 18–22° C. at a rate of 4–6° C. per min; and allowing the resulting sol-gel phase to stand at room temperature for 24–36 hours.

3. A method of using the composition of claim 1 to improve the growth and the preservation of bean plants, leaf vegetables and fruit vegetables by applying an effective amount of said composition to said plants or vegetables, said effective amount ranging from 0.1 to 0.3%.

* * * * *